United States Patent
Shalgi et al.

(10) Patent No.: US 7,688,064 B2
(45) Date of Patent: Mar. 30, 2010

(54) PROBE FOR ASSESSMENT OF METAL DISTORTION

(75) Inventors: Avi Shalgi, Tel-Aviv (IL); Ya'aeov Nitzan, Herzilya (IL)

(73) Assignee: Biosense Webster Inc., Diamond Bar, CA (US)

( * ) Notice: Subject to any disclaimer, the term of this patent is extended or adjusted under 35 U.S.C. 154(b) by 751 days.

(21) Appl. No.: 11/456,645

(22) Filed: Jul. 11, 2006

(65) Prior Publication Data

US 2008/0012553 A1 Jan. 17, 2008

(51) Int. Cl.
G01B 7/14 (2006.01)
G01R 35/00 (2006.01)

(52) U.S. Cl. .............. 324/207.12; 324/202; 324/207.17

(58) Field of Classification Search ........... 324/202, 324/207.11–207.18, 244, 261; 128/899; 600/117, 424

See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,767,669 A | 6/1998 | Hansen et al. | |
| 6,147,480 A | 11/2000 | Osadchy et al. | |
| 6,239,724 B1 | 5/2001 | Doron et al. | |
| 6,332,089 B1 | 12/2001 | Acker et al. | |
| 6,618,612 B1 | 9/2003 | Acker et al. | |
| 6,690,963 B2 | 2/2004 | Ben-Haim et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0165292 A1* | 7/2005 | Simon et al. | 600/407 |
| 2006/0105677 A1* | 5/2006 | Lin et al. | 451/5 |
| 2006/0241654 A1* | 10/2006 | Baldewein | 606/130 |

FOREIGN PATENT DOCUMENTS

WO WO 96/05768 A1 2/1996

* cited by examiner

*Primary Examiner*—Bot L LeDynh
(74) *Attorney, Agent, or Firm*—Louis J. Capezzuto

(57) ABSTRACT

Apparatus for assessing field distortion includes a probe and a processor. The probe includes a mechanical fixture for placement at a location to be tested, and one or more field generators, which are attached to the mechanical fixture and are arranged to generate respective magnetic fields. The probe further includes one or more field sensors, which are attached to the mechanical fixture at known positions with respect to the one or more field sensors and are arranged to sense the magnetic fields generated by the one or more field generators and to output signals responsively to the sensed magnetic fields. The processor is arranged to process the signals so as to assess a distortion of the magnetic fields sensed by the field sensors at the tested location.

24 Claims, 3 Drawing Sheets

PROBE FOR ASSESSMENT OF METAL DISTORTION

FIELD OF THE INVENTION

The present invention relates generally to magnetic position tracking systems, and particularly to methods and systems for assessing magnetic field distortion that affects position tracking measurements.

BACKGROUND OF THE INVENTION

Various methods and systems are known in the art for tracking the coordinates of objects involved in medical procedures. Some of these systems use magnetic field measurements. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations.

Additional methods and systems that relate to magnetic position tracking are also described, for example, in PCT Patent Publication WO 96/05768, U.S. Pat. Nos. 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. These publications describe methods and systems that track the position of intrabody objects such as cardiac catheters, orthopedic implants and medical tools used in different medical procedures.

It is well known in the art that the presence of metallic, paramagnetic or ferromagnetic objects within the magnetic field of a magnetic position tracking system often distorts the system's measurements. The distortion is sometimes caused by eddy currents that are induced in such objects by the system's magnetic field, as well as by other effects.

Various methods and systems have been described in the art for detecting field distortion and for performing position tracking in the presence of such distortion. For example, U.S. Pat. No. 6,147,480, whose disclosure is incorporated herein by reference, describes a method in which the signals induced in the tracked object are first detected in the absence of any articles that could cause parasitic signal components. Baseline phases of the signals are determined. When an article that generates parasitic magnetic fields is introduced into the vicinity of the tracked object, the phase shift of the induced signals due to the parasitic components is detected. The measured phase shifts are used to indicate that the position of the object may be inaccurate. The phase shifts are also used for analyzing the signals so as to remove at least a portion of the parasitic signal components.

As another example, U.S. Pat. No. 5,767,669, whose disclosure is incorporated herein by reference, describes a system for determining the position and orientation of remote sensors using pulsed magnetic fields. Pulsed magnetic fields are sequentially generated from a plurality of spatially independent components defining a source coordinate frame. The fields are sensed by a remote sensor having a plurality of passive field sensing elements. Eddy current distortions are sensed separately and subtracted by the system. The system measures the effect of metallic objects present in the environment and dynamically adjusts the measured values accordingly. The sensed magnetic fields, free of eddy current distortion, are used in order to calculate the position and orientation of the remote object.

SUMMARY OF THE INVENTION

Embodiments of the present invention provide methods and systems for assessing the level of field distortion caused by field-distorting objects, which is expected to affect the measurements of a magnetic position tracking system.

The distortion is assessed using a probe, which comprises one or more field generators and one or more field sensors attached at known positions to a common mechanical fixture. The probe is positioned at a tested location in order to assess the distortion level at this location. The field generators generate magnetic fields, which are sensed by the field sensors. The sensors produce signals responsively to the sensed fields. A processor processes the signals produced by the field sensors so as to assess the field distortion level at the tested location.

In some embodiments, the probe is pre-calibrated in free space to obtain reference, distortion-free field measurements. The processor calculates the deviation of the field measurements at the tested location from the corresponding reference measurements. If the deviation exceeds a predetermined threshold, the user is alerted.

Several probe configurations are described hereinbelow, such as linear configurations having multiple generator-sensor distances and planar configurations having multiple generator-sensor axis orientations.

The methods and systems described herein can be used when installing a magnetic position tracking system at a particular site, or during a medical procedure that involves magnetic position tracking.

There is therefore provided, in accordance with an embodiment of the present invention, apparatus for assessing field distortion, including:

a probe, including:

a mechanical fixture for placement at a location to be tested;

one or more field generators, which are attached to the mechanical fixture and are arranged to generate respective magnetic fields; and one or more field sensors, which are attached to the mechanical fixture at known positions with respect to the one or more field sensors and are arranged to sense the magnetic fields generated by the one or more field generators and to output signals responsively to the sensed magnetic fields; and a processor, which is arranged to process the signals so as to assess a distortion of the magnetic fields sensed by the field sensors at the tested location.

In an embodiment, the processor is arranged to assess the distortion by comparing the signals to reference values determined in the absence of the distortion. The probe may include a memory, which is arranged to hold the reference values. In another embodiment, the processor is arranged to alert a user when a deviation of the signals from the reference values exceeds a predetermined threshold.

In yet another embodiment, the one or more field generators and the one or more field sensors are arranged along a common axis.

In still another embodiment, the field generators and field sensors are arranged in at least two generator-sensor pairs, each of the pairs including one of the field generators and one of the field sensors separated by a respective distance, and at least two of the pairs have distances that are different from one another.

In an embodiment, the field generators and field sensors are arranged in at least two generator-sensor pairs, each of the pairs including one of the field generators and one of the field sensors arranged along a respective axis, and at least two of the pairs have axes oriented in different directions with respect to one another.

In some embodiments, one of the field generators is arranged to generate a first magnetic field having a first frequency, another of the field generators is arranged to generate a second magnetic field having a second frequency different from the first frequency, and at least one of the field sensors is arranged to sense the first and second magnetic fields simultaneously.

In another embodiment, the processor is arranged to evaluate an effect of the distortion on position measurements made by a magnetic position tracking system at the tested location.

In yet another embodiment, the magnetic position tracking system performs the position measurements using a field generator and a field sensor that are typically separated by a first distance, and at least one of the field generators and one of the field sensors of the probe are separated by a second distance that is selected so as to approximate the first distance.

In still another embodiment, the processor is arranged to determine a correction factor to be applied to the position measurements responsively to the assessed distortion.

In an embodiment, at least one of the field generators and the field sensors includes two or more coils arranged at different angular orientations with respect to one another.

In another embodiment, at least one of the field generators includes at least first and second field generating coils, which are oriented at respective different first and second angular orientations and are arranged to respectively generate first and second magnetic fields having different first and second frequencies, and at least one of the field sensors is arranged to sense the first and second magnetic fields simultaneously.

There is additionally provided, in accordance with an embodiment of the present invention, a method for assessing field distortion, including:

positioning a probe, which includes one or more field generators and one or more field sensors arranged in a fixed relative spatial relation, at a location to be tested;

while the probe is positioned at the location, actuating the one or more field generators to generate respective magnetic fields, and sensing the magnetic fields using the one or more field sensors so as to produce respective signals responsively to the sensed magnetic fields; and processing the signals so as to assess a distortion of the magnetic fields sensed by the field sensors at the tested location.

The present invention will be more fully understood from the following detailed description of the embodiments thereof, taken together with the drawings in which:

DETAILED DESCRIPTION OF EMBODIMENTS

Figure 1:
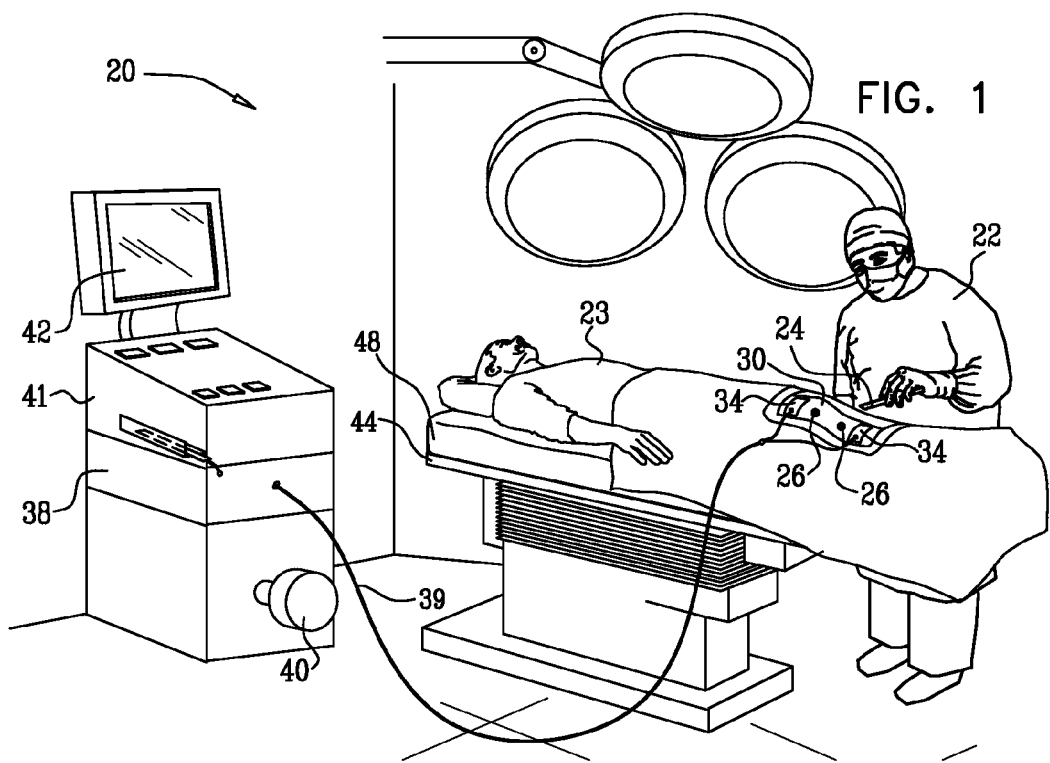
FIG. 1 is a schematic, pictorial illustration of a magnetic position tracking system used in surgery, in accordance with an embodiment of the present invention.

FIG. 1 is a schematic, pictorial illustration of a magnetic tracking system 20 used in surgery, in accordance with an embodiment of the present invention. A surgeon 22 performs a medical procedure on a patient 23 using a medical tool 24. Implants 26 are introduced into the patient's body at a surgical site, which is located in this example in a leg 30 of the patient. The tracking system guides the surgeon in performing the procedure, in this example a knee-joint operation, by measuring and presenting the positions of implants 26 and tool 24. The system measures the location and orientation coordinates throughout a working volume that comprises the surgical site.

The coordinates of tool 24 and implants 26 are determined relative to field generators, such as location pads 34, which are fixed to the patient's body. As can be appreciated, the field generators have floating coordinates, i.e., the location pads may not be fixed in space. In the example shown in FIG. 1, the pads are placed on the patient's calf and thigh, in proximity to implants 26. A console 38 generates drive signals that drive the field generators, typically comprising field generating coils, in location pads 34. The field generators generate magnetic fields throughout the working volume. Console 38 is connected to location pads 34 using a cable 39.

Implants 26 and tool 24 typically contain miniature, wireless sensor units. Each sensor unit comprises a field sensor that is designed to sense the magnetic field in its vicinity. The magnetic fields generated by location pads 34 induce currents in the field sensors of the sensor units fitted into tool 24 and implants 26. In response to the induced currents, signal processing and transmitter circuits in each sensor unit generate and transmit position signals that are indicative of the location and orientation of the implant or tool.

The position signals are received by a wireless control unit 40, which is coupled to a computer 41. Computer 41 serves as the main system controller of system 20. The computer processes the received signals in order to calculate the relative location and orientation coordinates of tool 24 and/or implants 26. The results are typically presented to the surgeon on a display 42.

Patient 23 lies on an operating table 44, which is typically metallic or has significant metallic content. As noted above, the presence of metallic and other field-distorting objects in or near the working volume of system 20 often distorts the magnetic field generated by the system. As a result, the position measurements performed by the system may be distorted. It is therefore desirable to keep such field distorting objects as far away as practically feasible from the working volume.

For example, in some installations of system 20, a mattress 48 is placed between patient 23 and table 44. In addition to padding the operating table for the comfort of the patient, mattress 48 increases the separation between the operating table and the working volume of system 20. A thicker mattress causes location pads 34, tool 24 and implants 26 to be located further away from the metallic operating table, thus reducing the level of field distortion.

Although the exemplary embodiment of FIG. 1 refers to an orthopedic surgery application, the methods and systems described herein can be used to assess field distortion levels in any other magnetic position tracking application, such as, for example, cardiac catheterization procedures. In general, the methods and systems described herein can be used to assess distortion caused by any object, regardless of whether it is related to the position tracking system.

Figure 2:
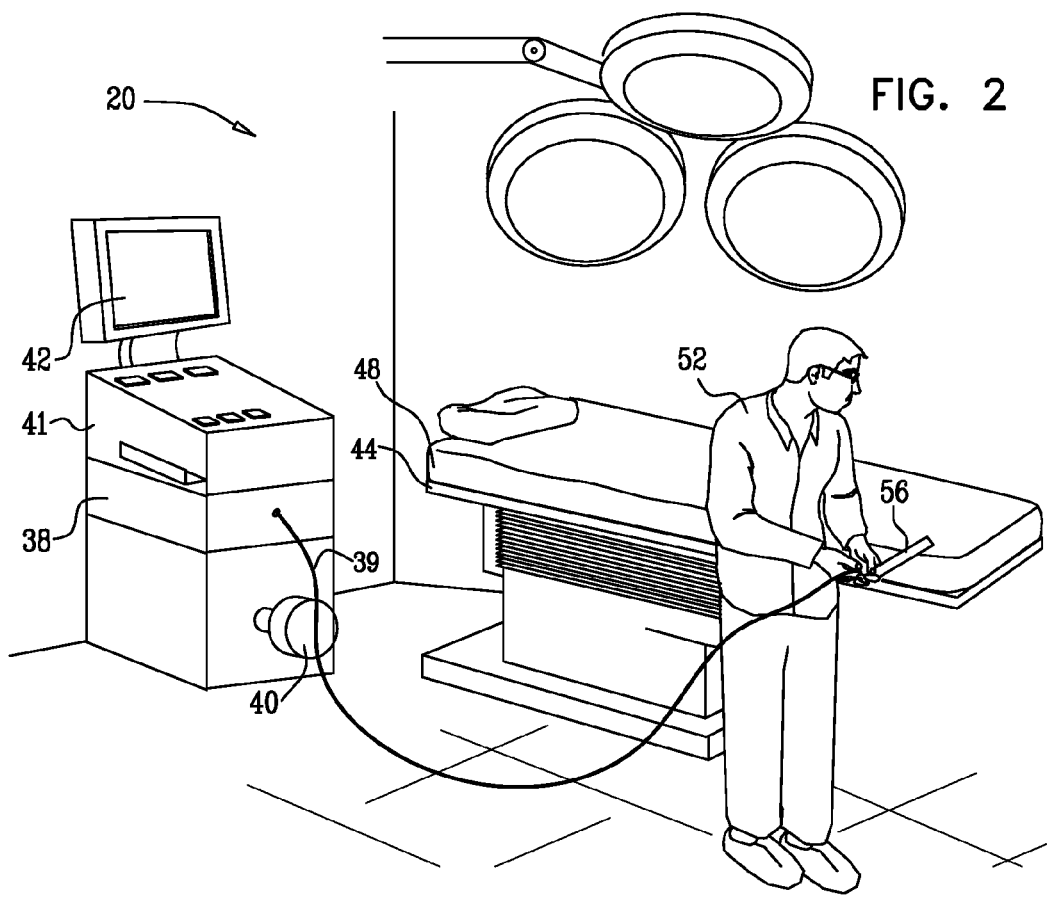
FIG. 2 is a schematic, pictorial illustration of an installation procedure of a magnetic position tracking system, in accordance with an embodiment of the present invention.

FIG. 2 is a schematic, pictorial illustration of an installation procedure of system 20, in accordance with an embodiment of the present invention. An installer, such as a field service technician 52, installs system 20 at a particular operating room. As part of the system installation, technician 52 verifies that the level of field distortion caused by metallic objects in the working volume of the system is acceptable.

Technician 52 uses a distortion assessment probe 56 to measure and assess the distortion levels, which are expected to affect the position measurements of system 20 in subsequent medical procedures. The structure and functionality of probe 56 will be described in detail hereinbelow. In principle, probe 56 comprises one or more field generators and one or more field sensors, which are attached to a mechanical fixture at known relative positions. The probe is connected to console 38 by a cable 58.

Probe 56 is pre-calibrated in free space, i.e., without the presence of field-distorting elements. In the calibration process, each of the probe's field generators is driven to produce a magnetic field. The magnetic field of each field generator is sensed by each of the probe's field sensors. The field measurements of each generator-sensor pair are stored as reference measurements.

Pre-calibration of probe 56 is typically carried out as part of the manufacturing of the probe, and not at the installation site. The reference field measurements are associated with the probe and not with any particular installation of system 20. Thus, the reference measurements can be stored in a non-volatile memory device attached to the probe and readable by computer 41. Alternatively, the reference measurements can be supplied with the probe and stored in system 20, for example in a memory of computer 41.

In order to assess the expected distortion at a particular tested location, technician 52 holds probe 56 at this location. Console 38 drives the field generators in probe 56 with drive signals, which generate respective magnetic fields. The field sensors in the probe sense the generated fields and produce respective position signals. The position signals are sent to console 38 via cable 58. Computer 41 analyzes the position signals and estimates the level of field distortion at the tested location.

Computer 41 compares the field strength measurements at the tested location with the reference measurements obtained in the calibration process. The deviation of the field measurements at the tested location from the reference measurements is indicative of the expected distortion level at the tested location. Typically, the deviation is defined as the vector difference between a field measured at the tested location and the corresponding reference measurements, thus taking into account both field strength and phase differences. The deviation may be calculated separately for each pair of field generator and field sensor. Alternatively, a composite deviation value, such as the sum of the deviations over all generator-sensor pairs, can be used.

Alternatively, computer 41 may calculate the location coordinates of the probe's field sensors with respect to its field generators. These coordinates can be compared with reference location coordinates based on free space measurements.

In some embodiments, the technician is alerted if the deviation exceeds a predetermined threshold, such as by a message displayed on display 42 or using any other suitable means.

The technician may scan the probe over multiple tested locations so as to map the expected distortion levels in the vicinity of the operating table. In particular, the technician can use probe 56 to determine whether the thickness of mattress 48 is sufficient. If the distortion levels above the mattress are unacceptable, a thicker mattress may be used.

Additionally or alternatively, other measures can be taken based on the assessed distortion. For example, computer 41 may use the deviation to calculate a correction factor that should be applied to subsequent position measurements performed by the position tracking system at the tested location. Since the correction factor values tend to vary significantly with location, determining the correction factor should be performed when the location coordinates of the probe are known to be accurate, such as using a suitable robot that maps the working volume.

Figure 3A:
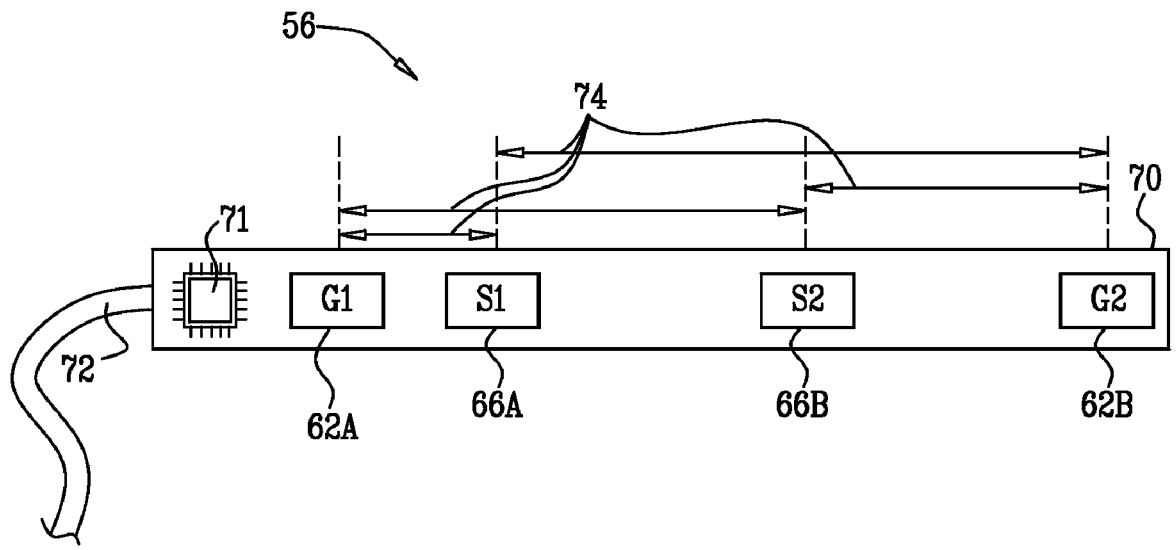
FIGS. 3A and 3B are diagrams that schematically illustrate probes for assessing magnetic field distortion, in accordance with embodiments of the present invention.

FIG. 3A is a diagram that schematically illustrates an exemplary configuration of probe 56, in accordance with an embodiment of the present invention. In the configuration of FIG. 3A, probe 56 comprises two field generators 62A and 62B and two field sensors 66A and 66B, attached to a mechanical fixture 70 at known locations along a common axis. Field generators 62A and 62B are typically similar to the field generators fitted into location pads 34, and field sensors 66A and 66B are typically similar to the field sensors fitted into tool 24 and implants 26. The field generators and field sensors are connected to console 38 by a cable 72.

In some embodiments, each of the field generators may comprise multiple field generating coils, which are oriented at different planes so as to generate magnetic fields having different orientations. For example, each field generator may comprise three mutually-orthogonal field generating coils. Similarly, the field sensors may also comprise multiple field sensing coils having different orientations, in order to simultaneously sense multiple magnetic field components. Using such a configuration, the probe can simultaneously assess the field distortion associated with magnetic fields having different orientations.

In some embodiments, probe 56 comprises a non-volatile memory device 71, such as a programmable read only memory (PROM) or flash memory device, in which the reference measurements are stored following the free space calibration process. Computer 41 can read the contents of memory 71 via cable 72.

In many practical cases, the level of field distortion in a particular measurement depends on the distance between the field generator and the field sensor. Thus, performing field measurements at different generator-sensor distances provides additional information regarding the distortion and improves the reliability of the distortion assessment.

In order to provide measurements at multiple generator-sensor distances, the field generators and field sensors of probe 56 are distributed at uneven distances along the common axis. Since probe 56 comprises two field generators and two field sensors, there are four possible generator-sensor pairs 74. As can be seen in the figure, in the present example all four distances are different from one another.

In some cases, the generator-sensor distances which will be used by system 20 in the medical procedure are known, either accurately or approximately. For example, when conducting the knee-joint procedure shown in FIG. 1, the distances between location pads 34 and implants 26 are known a-priori. In such cases, the generator-sensor distances in probe 56 can be selected so as to match the distances that will subsequently be used in the medical procedure itself. (Alternatively, given a particular probe, location pads 34 can be placed so that their distances from the implants match the probe generator-sensor distances.) Using similar generator-sensor distances in the distortion assessment and in the medical procedure increases the accuracy of the assessment.

In some embodiments, the measurement time at each tested location can be reduced by assigning different frequencies to the field generators of the probe. In these embodiments, the field sensors sense the magnetic fields generated by the different field generators simultaneously. Because of the use of different frequencies, computer 41 can filter the resulting position signals and resolve the contribution of each individual field generator. When using field generators comprising multiple field generating coils, each coil is typically assigned a different frequency.

In alternative embodiments, any other suitable probe configuration comprising one or more field generators and one or more field sensors can be used.

Figure 3B:
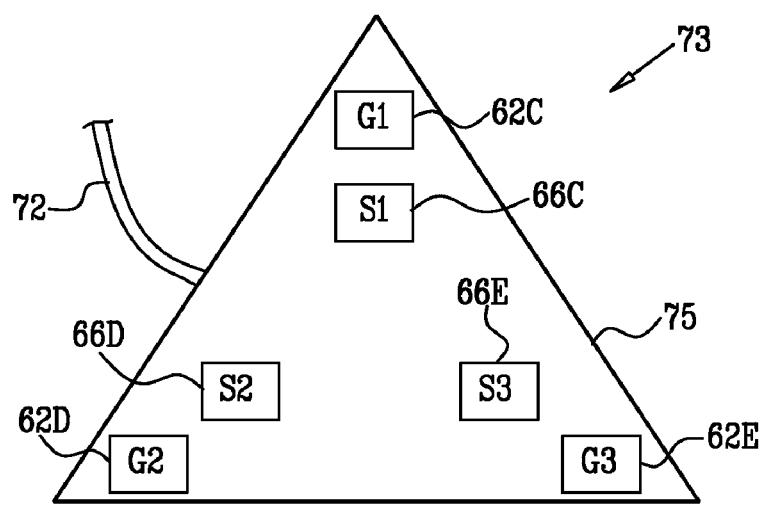

FIG. 3B is a diagram that schematically illustrates an alternative probe 73 for assessing magnetic field distortion, in accordance with another embodiment of the present invention. In some practical cases, the distortion level varies with the orientation of the axis connecting the field generator and field sensor. In such cases, in order to obtain adequate distortion mapping, probe 56 of FIG. 3A above would have to be rotated through multiple orientations at each tested location, which complicates the assessment process and increases the measurement time.

In order to obtain field measurements at multiple orientations and locations, probe 73 comprises three field generators denoted 62C, 62D and 62E, and three field sensors denoted 66C, 66D and 66E, typically located at uneven positions. The field generators and field sensors are arranged in a triangular configuration and attached to a mechanical fixture 75. In the present example, probe 73 comprises nine possible generator-sensor pairs arranged along multiple axes that are different from one another. When placed at a particular tested location, probe 73 simultaneously produces field measurements at multiple orientations by using different generator-sensor pairs.

The triangular configuration of probe 73 is an exemplary configuration, chosen purely for the sake of conceptual clarity. Any other suitable probe configuration, which comprises at least two different generator-sensor axes, can be used. Such configurations may be planar (i.e., two-dimensional) or three-dimensional. Hybrid configurations having both multiple generator-sensor distances and multiple generator-sensor axes can also be used.

Figure 4:
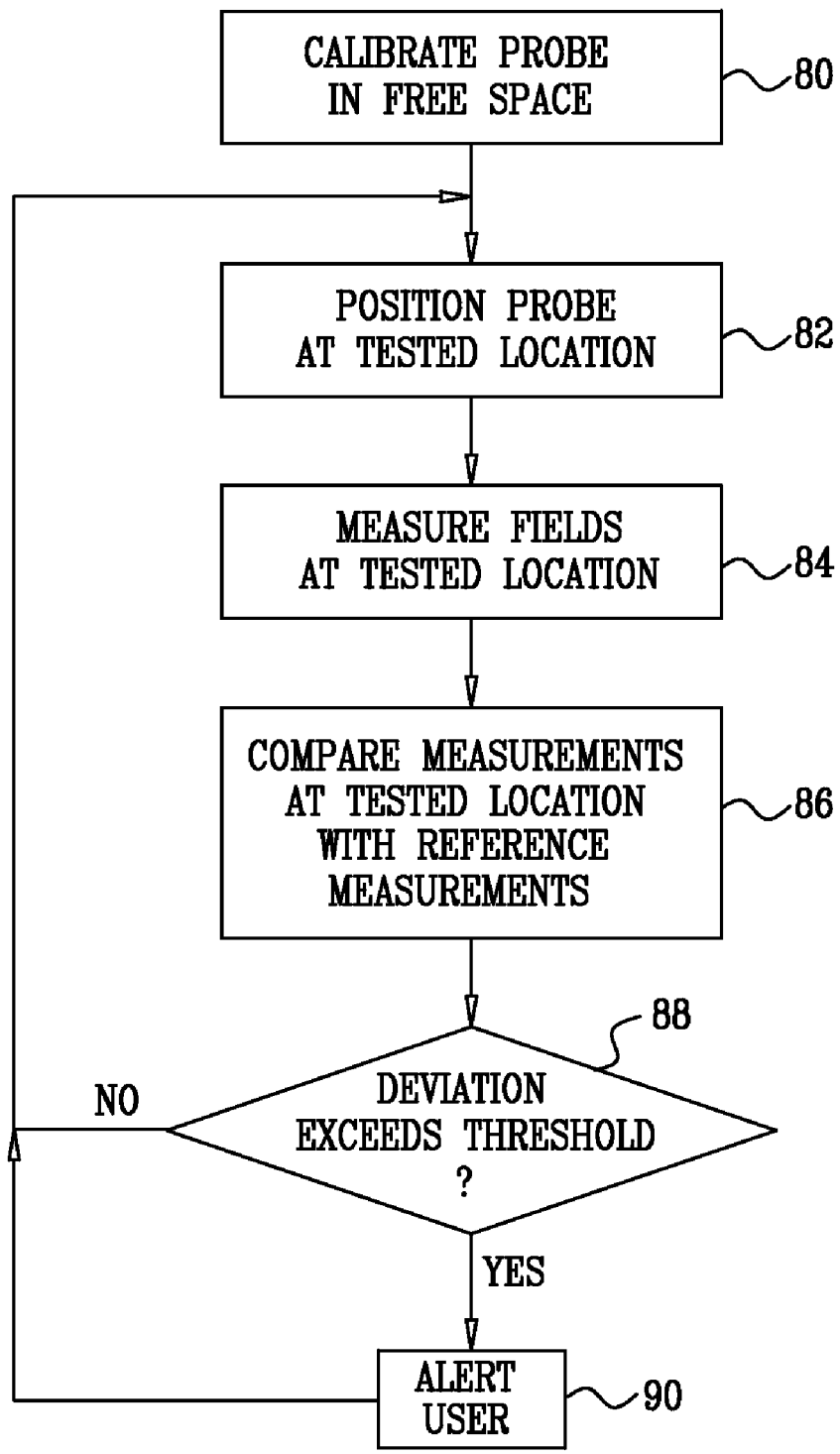
FIG. 4 is a flow chart that schematically illustrates a method for assessing magnetic field distortion, in accordance with an embodiment of the present invention.

FIG. 4 is a flow chart that schematically illustrates a method for assessing magnetic field distortion, in accordance with an embodiment of the present invention. The method begins by calibrating the distortion assessment probe in free space, at a pre-calibration step 80. As noted above, reference field measurements are performed, typically during probe production, and the reference measurements provided to computer 41.

When evaluating a particular installation site of system 20, the technician positions the probe at a certain tested location, at a positioning step 82. System 20 measures the magnetic fields of the different generator-sensor pairs of the probe, at a measurement step 84. Computer 41 compares the fields measured at the tested location with the corresponding reference measurements, at a comparison step 86. Computer 41 calculates the deviation of the field measurements at the tested location from the reference measurements.

If the deviation exceeds a predefined threshold, as checked at a checking step 88, computer 41 alerts the technician, at an alerting step 90. Otherwise, the tested location is assumed to have a tolerable level of distortion. The method then loops back to positioning step 82 above, and the technician continues to assess other tested locations.

Although the embodiments described herein mainly address distortion caused by a metallic operating table, the methods and systems described herein can be used to assess distortion caused by any other field-distorting objects in the vicinity of system 20, such as various metallic medical and surgical tools and instruments. Additionally or alternatively, the methods and systems described herein can be carried out before the medical procedure, either by the physician performing the procedure or by another person. For example, a distortion assessment probe can be mounted at a fixed location in the working volume in order to monitor the distortion level at this location over time. It is typically recommended to perform the distortion assessment before the surgery, so that the probe does not have to be sterilized.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. Apparatus for assessing field distortion, comprising:
    a moveable probe, comprising:
        a mechanical fixture for placement at a location to be tested;
        one or more field generators, which are attached to the mechanical fixture and are arranged to generate respective magnetic fields; and
        one or more field sensors, which are attached to the mechanical fixture at known positions with respect to the one or more field sensors and are arranged to sense the magnetic fields generated by the one or more field generators and to output signals responsively to the sensed magnetic fields, the output signals including position signals and magnetic field strength signals; and
    a processor of a computer, which is arranged to process the output signals so as to assess a distortion of the magnetic fields sensed by the field sensors at the tested location including estimating a level of the distortion.

2. The apparatus according to claim 1, wherein the processor is arranged to assess the distortion by comparing the output signals to reference values determined in the absence of the distortion.

3. The apparatus according to claim 2, wherein the probe comprises a memory, which is arranged to hold the reference values.

4. The apparatus according to claim 2, wherein the processor is arranged to alert a user when a deviation of the output signals from the reference values exceeds a predetermined threshold.

5. The apparatus according to claim 1, wherein the one or more field generators and the one or more field sensors are arranged along a common axis.

6. The apparatus according to claim 1, wherein the field generators and field sensors are arranged in at least two generator-sensor pairs, each of the pairs comprising one of the field generators and one of the field sensors separated by a respective distance, and wherein at least two of the pairs have distances that are different from one another.

7. The apparatus according to claim 1, wherein the field generators and field sensors are arranged in at least two generator-sensor pairs, each of the pairs comprising one of the field generators and one of the field sensors arranged along a respective axis, and wherein at least two of the pairs have axes oriented in different directions with respect to one another.

8. The apparatus according to claim 1, wherein one of the field generators is arranged to generate a first magnetic field having a first frequency, wherein another of the field generators is arranged to generate a second magnetic field having a second frequency different from the first frequency, and wherein at least one of the field sensors is arranged to sense the first and second magnetic fields simultaneously.

9. The apparatus according to claim 1, wherein the processor is arranged to evaluate an effect of the distortion on position measurements made by a magnetic position tracking system at the tested location.

10. The apparatus according to claim 9, wherein the magnetic position tracking system performs the position measurements using a field generator and a field sensor that are typically separated by a first distance, and wherein at least one of the field generators and one of the field sensors of the probe are separated by a second distance that is selected so as to approximate the first distance.

11. The apparatus according to claim 9, wherein the processor is arranged to determine a correction factor to be applied to the position measurements responsively to the assessed distortion.

12. The apparatus according to claim 1, wherein at least one of the field generators comprises at least first and second field generating coils, which are oriented at respective different first and second angular orientations and are arranged to respectively generate first and second magnetic fields having different first and second frequencies, and wherein at least one of the field sensors is arranged to sense the first and second magnetic fields simultaneously.

13. A method for assessing field distortion, comprising:
positioning a moveable probe, which includes one or more field generators and one or more field sensors arranged in a fixed relative spatial relation, at a location to be tested;
while the probe is positioned at the location, actuating the one or more field generators to generate respective magnetic fields, and sensing the magnetic fields using the one or more field sensors so as to produce respective output signals responsively to the sensed magnetic fields, the output signals including position signals and magnetic field strength signals; and
processing the output signals using a computer so as to assess a distortion of the magnetic fields sensed by the field sensors at the tested location including estimating a level of the distortion.

14. The method according to claim 13, wherein processing the output signals comprises comparing the output signals to reference values determined in the absence of the distortion.

15. The method according to claim 14, wherein the reference values are stored in a memory of the probe, and wherein comparing the output signals to the reference values comprises reading the reference values from the memory.

16. The method according to claim 14, wherein processing the output signals comprises alerting a user when a deviation of the output signals from the reference values exceeds a predetermined threshold.

17. The method according to claim 13, wherein the one or more field generators and the one or more field sensors are arranged along a common axis.

18. The method according to claim 13, wherein the field generators and field sensors are arranged in at least two generator-sensor pairs, each of the pairs comprising one of the field generators and one of the field sensors separated by a respective distance, and wherein at least two of the pairs have distances that are different from one another.

19. The method according to claim 13, wherein the field generators and field sensors are arranged in at least two generator-sensor pairs, each of the pairs comprising one of the field generators and one of the field sensors arranged along a respective axis, and wherein at least two of the pairs have axes oriented in different directions with respect to one another.

20. The method according to claim 13, wherein actuating the one or more field generators comprises generating a first magnetic field having a first frequency from one of the field generators, and generating a second magnetic field having a second frequency different from the first frequency by another of the field generators, and wherein sensing the magnetic fields comprises sensing the first and second magnetic fields simultaneously by at least one of the field sensors.

21. The method according to claim 13, wherein processing the output signals comprises evaluating an effect of the distortion on position measurements made by a magnetic position tracking system at the tested location.

22. The method according to claim 21, wherein the magnetic position tracking system performs the position measurements using a field generator and a field sensor that are typically separated by a first distance, and wherein at least one of the field generators and one of the field sensors of the probe are separated by a second distance that is one of the field generators at least first and second magnetic selected so as to approximate the first distance.

23. The method according to claim 21, wherein processing the output signals comprises determining a correction factor to be applied to the position measurements responsively to the assessed distortion.

24. The method according to claim 13, wherein actuating the one or more field generators comprises generating from one of the field generators at least first and second magnetic fields having respective different first and second angular orientations and respective different first and second frequencies, and wherein sensing the magnetic fields comprises sensing the first and second magnetic fields simultaneously by at least one of the field sensors.

* * * * *